(12) United States Patent
McCormick

(10) Patent No.: US 10,378,695 B2
(45) Date of Patent: Aug. 13, 2019

(54) CRYOGENIC STORAGE CONTAINER

(71) Applicant: Savsu Technologies LLC, Old Bethpage, NY (US)

(72) Inventor: Bruce McCormick, Santa Fe, NM (US)

(73) Assignee: SAVSU TECHNOLOGIES LLC, Old Bethpage, NY (US)

( * ) Notice: Subject to any disclaimer, the term of this patent is extended or adjusted under 35 U.S.C. 154(b) by 67 days.

(21) Appl. No.: 15/605,367

(22) Filed: May 25, 2017

(65) Prior Publication Data
US 2017/0343264 A1    Nov. 30, 2017

Related U.S. Application Data

(60) Provisional application No. 62/341,413, filed on May 25, 2016.

(51) Int. Cl.
| | | |
|---|---|---|
| *F17C 3/08* | (2006.01) | |
| *F17C 13/00* | (2006.01) | |
| *F25D 3/10* | (2006.01) | |
| *A01N 1/02* | (2006.01) | |

(52) U.S. Cl.
CPC ............ *F17C 3/08* (2013.01); *A01N 1/0257* (2013.01); *F17C 13/001* (2013.01); *F25D 3/107* (2013.01); *F17C 2203/0333* (2013.01); *F17C 2203/0366* (2013.01); *F17C 2203/0626* (2013.01); *F17C 2221/033* (2013.01); *F17C 2250/0439* (2013.01)

(58) Field of Classification Search
CPC .......... F17C 3/085; F17C 3/08; F17C 13/001; F17C 13/00; B65D 81/3816; B65D 81/3823; B65D 81/3874; B65D 81/38; B65D 25/14; B65D 1/40; F25D 3/107; A01N 1/0257
USPC ............ 220/560.12, 560.14, 560.15, 592.25, 220/592.26, 592.2, 62.22, 62.11, DIG. 9; 62/60; 206/545; 428/36.5, 36.6, 35.7, 428/613
See application file for complete search history.

(56) References Cited

U.S. PATENT DOCUMENTS

| | | | | |
|---|---|---|---|---|
| 2,106,828 A | * | 2/1938 | Chappell | B05D 7/22 220/62.11 |
| 2,897,657 A | * | 8/1959 | Rupp | B63B 25/16 114/74 A |
| 3,215,313 A | * | 11/1965 | Stelts | F17C 13/088 220/560.13 |
| 3,261,087 A | * | 7/1966 | Schlumberger | E01C 11/106 156/160 |
| 3,420,363 A | * | 1/1969 | Blickensderfer | B65D 81/1275 206/524 |
| 3,765,558 A | * | 10/1973 | Withers | B29C 70/08 220/560.15 |

(Continued)

*Primary Examiner* — Robert J Hicks
(74) *Attorney, Agent, or Firm* — Reising Ethington P.C.

(57) ABSTRACT

A portable cryogenic container includes a porous material configured to absorb a cryogenic coolant such as liquid nitrogen. The coolant-absorbing material at least partially defines a storage cavity in the container that is configured to accept and support a cassette or other type of contents container in which a product to be cryogenically stored is contained. With cryogenic coolant absorbed into the container, the temperature within the storage cavity can be maintained sufficiently close to the boiling point of the cryogenic coolant to preserve post-thaw viability of the stored product for several hours.

21 Claims, 3 Drawing Sheets

(56) References Cited

U.S. PATENT DOCUMENTS

| | | | | |
|---|---|---|---|---|
| 4,835,975 | A * | 6/1989 | Windecker | F17C 1/14 220/560.05 |
| 5,060,481 | A * | 10/1991 | Bartlett | F17C 13/026 137/341 |
| 5,386,706 | A * | 2/1995 | Bergsten | C04B 30/00 220/560.12 |
| 6,087,581 | A * | 7/2000 | Emmer | F17C 3/08 174/17 R |
| 6,209,343 | B1 * | 4/2001 | Owen | A01N 1/02 252/67 |
| 6,655,156 | B1 * | 12/2003 | Miksic | F17C 1/00 220/560.04 |
| 7,299,650 | B1 * | 11/2007 | Romanos | F17C 3/085 62/371 |
| 2002/0065627 | A1 * | 5/2002 | Neeser | F17C 13/025 702/156 |
| 2002/0084277 | A1 * | 7/2002 | Mullens | F17C 3/08 220/560.04 |
| 2004/0091654 | A1 * | 5/2004 | Kelly | B01D 35/30 428/35.7 |
| 2015/0345691 | A1 * | 12/2015 | Sagnard | F16L 59/153 428/36.5 |
| 2016/0318694 | A1 * | 11/2016 | Mitchell | A45C 11/20 |
| 2018/0022073 | A1 * | 1/2018 | Sasaki | B32B 27/00 428/35.7 |
| 2018/0112823 | A1 * | 4/2018 | Ducloy | F17C 3/027 |

* cited by examiner

CRYOGENIC STORAGE CONTAINER

TECHNICAL FIELD

The present disclosure relates generally to insulated storage containers and, in particular, to cryogenic storage containers.

BACKGROUND

Life science products are often kept in cryogenic freezers or dewars to maintain post-thaw viability. When these products are needed for use, such as in cell therapy treatment, such materials may be removed from the cryogenic freezer and transferred to a portable dewar to accommodate transport and delivery of the materials to the bedside of the patient while continuing to maintain the desired cryogenic temperature, such as about −196° C. when using liquid nitrogen as thermal mass within the dewar. However, preparation and transport of such dewars from a cryogenic freezer to the patient bedside is no simple matter, as these types of dewars are typically large and heavy. These portable dewars may also require temperature conditioning as much as 24 hours prior to use, which can further complicate and limit their utility.

SUMMARY

In accordance with one or more embodiments, a cryogenic storage container includes one or more walls that together define a closable storage cavity, wherein at least one of the walls comprises a layer of porous material configured to absorb a cryogenic coolant and to release the cryogenic coolant in vapor form into the storage cavity.

In some embodiments, the cryogenic storage container includes a super-insulating layer, and the layer of porous material is located between the super-insulating layer and the storage cavity.

In some embodiments, the cryogenic storage container includes a layer of material that is super-insulating at atmospheric pressure, and the layer of porous material is located between the layer of super-insulating material and the storage cavity.

In some embodiments, the layer of porous material comprises calcium silicate.

In some embodiments, the layer of porous material comprises a super-insulating material.

In some embodiments, the layer of porous material has a non-uniform thickness.

In some embodiments, the layer of porous material has a thickness at an open end of the storage cavity that is greater than a thickness at a closed end of the storage cavity.

In some embodiments, the layer of porous material is removable and replaceable.

In some embodiments, the cryogenic storage container includes a layer of super-insulating material encapsulated in a foam material, and the layer of porous material defines at least a portion of the storage cavity and is located between the storage cavity and the encapsulated super-insulating material.

In some embodiments, the cryogenic storage container includes a layer of aerogel material encapsulated in a polyurethane foam material, and the layer of porous material comprises calcium silicate and is located between the storage cavity and the encapsulated aerogel material.

In some embodiments, the cryogenic storage container includes a fluid barrier layer configured to contain the cryogenic coolant within the layer of porous material and/or within the storage cavity.

In some embodiments, the cryogenic storage container does not include a vacuum panel.

In some embodiments, the cryogenic storage container includes a data storage device and/or a locator device.

In some embodiments, the cryogenic storage container includes a temperature sensor adapted to measure the temperature of the cavity and extending at least partially through one of the walls.

In some embodiments, the cryogenic storage container includes a retraction device adapted to remove a cassette from the storage cavity.

In some embodiments, the cryogenic storage container includes a vent configured to permit the cryogenic coolant to be transported from the storage cavity to a location outside the storage container when there is cryogenic coolant in the storage container, the storage cavity is closed, and the pressure inside the storage cavity exceeds a threshold value.

In some embodiments, the layer of porous material has a porosity of at least 75%.

In some embodiments, the layer of porous material is formed from a non-polymeric or inorganic material.

In accordance with one or more embodiments, a method of cryogenically storing a product includes the step of housing the product in a storage cavity of a portable storage container comprising a cryogenic coolant absorbed by a wall that at least partially defines the storage cavity.

In some embodiments, the method includes the step of introducing the cryogenic coolant to a porous layer of the wall while the porous layer is attached to the portable storage container and before the product is housed in the storage cavity.

In some embodiments, the method includes the step of assembling a porous layer to a portion of a storage container comprising a super-insulating layer, wherein the porous layer includes the absorbed cryogenic coolant during the step of assembling.

Within the scope of this application it is envisaged that the various aspects, embodiments, examples, features and alternatives set out in the preceding paragraphs, in the claims and/or in the following description and drawings may be taken independently or in any combination thereof, except where there is incompatibility of features.

BRIEF DESCRIPTION OF THE DRAWINGS

One or more embodiments of the invention will hereinafter be described in conjunction with the appended drawings, wherein like designations denote like elements, and wherein.

DESCRIPTION OF ILLUSTRATIVE EMBODIMENTS

Described below is a portable cryogenic container that includes a porous material configured to absorb a cryogenic coolant such as liquid nitrogen. The coolant-absorbing material at least partially defines a storage cavity in the container that is configured to accept and support a cassette or other type of contents container in which a product to be cryogenically stored is contained. With cryogenic coolant absorbed into the container, the temperature within the storage cavity can be maintained sufficiently close to the boiling point of the cryogenic coolant to preserve post-thaw viability of the stored product for several hours. For instance, with liquid nitrogen as the cryogenic coolant having a boiling point of $-196°$ C., the cavity of the cryogenic container described below can be maintained at about $-150°$ C. for several hours, which is a sufficiently low temperature for many life science products to be kept prior to use. A retraction device configured to place or remove a storage cassette from the cavity is also described.

Figure 1:
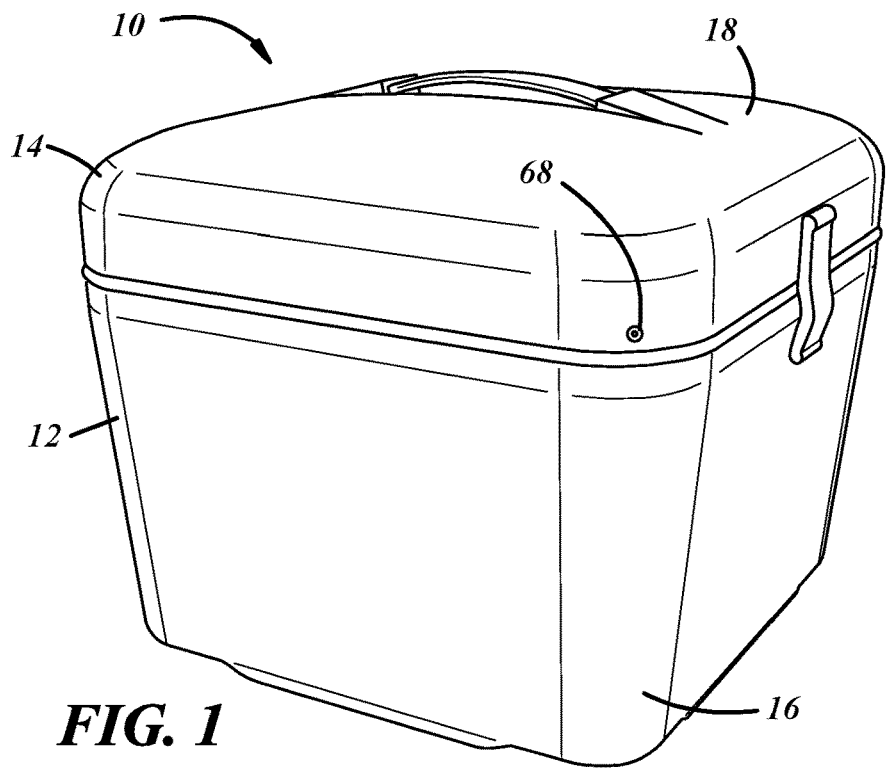
FIG. 1 is a perspective view of an illustrative portable cryogenic storage container in a closed condition.

FIG. 1 illustrates an example of a portable cryogenic container 10 including a bottom 12 and a removable top or lid 14. Only the exterior of the container 10 is shown in FIG. 1, in which a portion of a shell 16, 18 is visible for both the bottom 12 and the top 14. A handle is provided to carry the container when in the illustrated closed and latched condition or to remove and replace the lid 14, and one or more latches may be provided as shown to releasably attach the bottom 12 and the lid 14 together.

Figure 2:
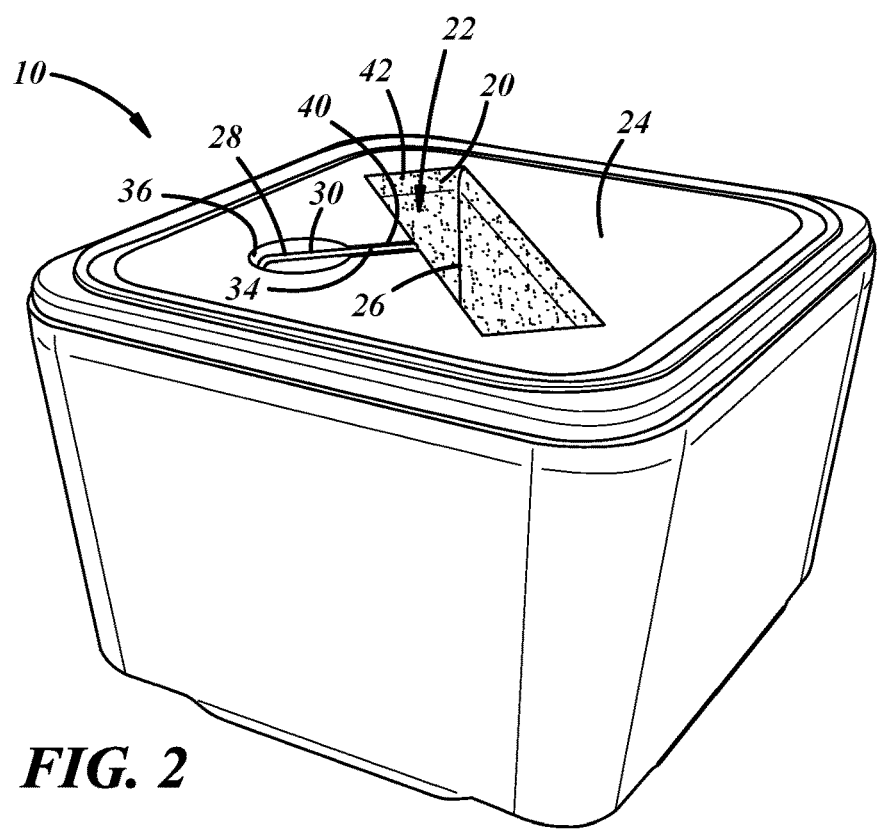
FIG. 2 is the perspective view of the storage container of FIG. 1 in an open condition with a lid of the container removed.

FIG. 2 illustrates the container 10 of FIG. 1 with the lid removed to reveal an open end 20 of a storage cavity 22 formed in an upper face 24 of the bottom 12 of the container. The illustrated storage cavity 22 has a rectangular open end 20 and may be lined with and/or at least partially defined by a layer 26 of porous material configured to absorb a cryogenic coolant within its pores and to release the cryogenic coolant in vapor form into the storage cavity 22. As used herein, a cryogenic coolant is a substance with a boiling point of about $-150°$ C. or less that is used at a temperature at or below its boiling point. As noted above, liquid nitrogen is an example of a cryogenic coolant. Other examples include liquefied helium, hydrogen, neon, nitrogen, oxygen, or air.

The illustrated container 10 also includes a retraction device 28 configured to remove a cassette or other contents container (not shown) from the storage cavity 22. The illustrated retraction device 28 includes a handle 30, a cassette support 32 (FIG. 4), and a connector 34 extending between the handle 30 and the cassette support 32. The handle 30 fits into a recess 36 formed in the upper face 24 of the container bottom 12, the support 32 is located at a closed end 38 (FIGS. 3 and 4) of the storage cavity 22 (i.e., under the cassette when the cassette is in the cavity), and the connector 34 extends along a groove or recess 40 formed in the upper face 24 and/or a wall inner surface 42 surrounding the storage cavity 22. The handle 30 is configured to be manually grasped, with the recess 36 providing clearance for fingers and/or a portion of the handle. Lifting the handle 30 away from the bottom 12 results in the support 32 being moved away from the closed end 38 and toward the open end 20 of the storage cavity 22, along with the cassette supported thereby. In this example, the retraction device 28 is formed from a bent rod having a constant cross section, but the device 28 can take many forms, as can its subcomponents.

Figure 3:
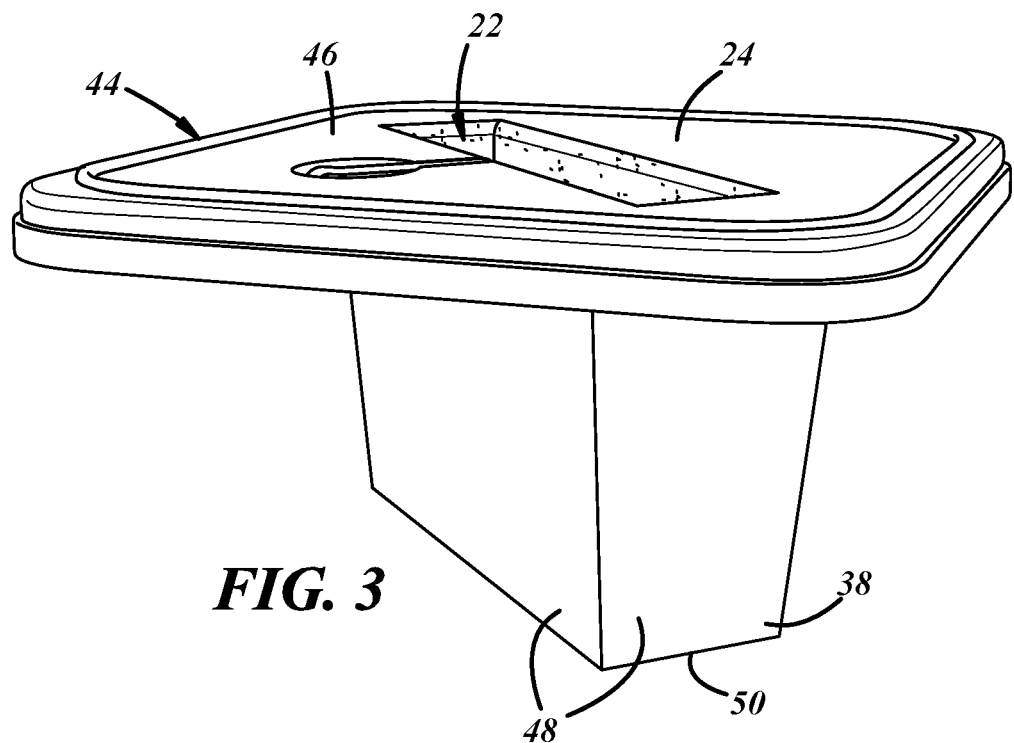
FIG. 3 is a perspective side view of a portion of the storage container of FIGS. 1 and 2 including a porous layer configured to absorb a cryogenic coolant.
Figure 4:
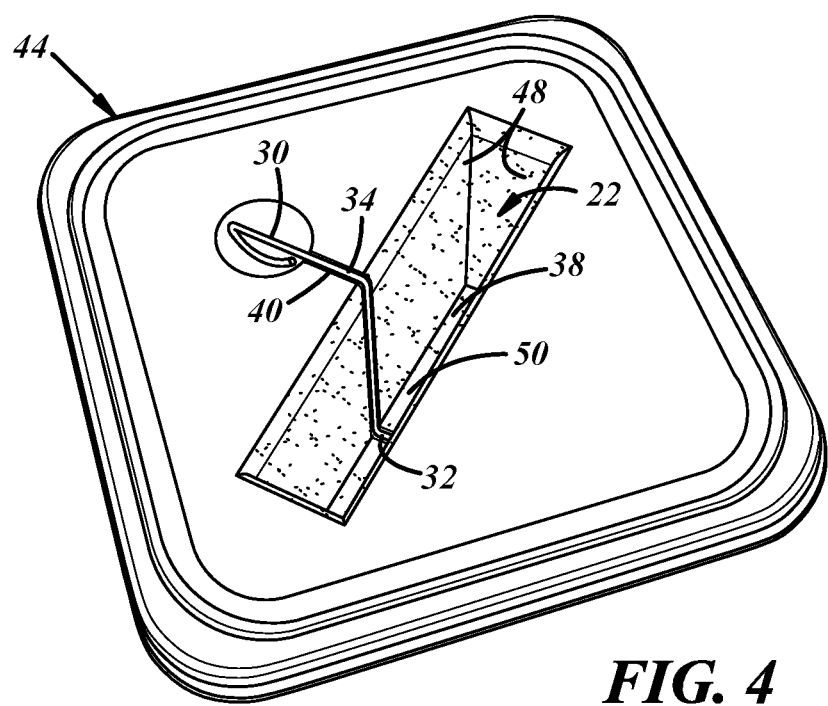
FIG. 4 is a perspective top view of the storage container portion of FIG. 3.

FIG. 3 illustrates a first portion 44 of the bottom 12 of the container 10, including an upper shell portion 46 and one or more walls 48 extending from a side of the shell portion 46 opposite the upper face 24. The one or more walls 48, in this case four sidewalls, together circumscribe and partly define the storage cavity 22. A bottom wall 50 (FIG. 5) also partly defines the cavity 22 at the closed end 38. The cavity may be considered to be defined by a single wall, for example where there are no corners as with a dish-shaped cavity. At least one of the one or more walls 48, 50 includes the layer of porous material 26. In this case, each of the four sidewalls 48 and the bottom wall 50 is formed from the porous material, but any or all of the walls may include other layers or additional materials. The porous material defines some portion of the cavity 22 such that liquid cryogenic coolant can be absorbed by the porous material from the cavity 22 and emitted by the porous material to the cavity 22 in vapor form. FIG. 4 illustrates the same portion 44 of the bottom of the container shown in FIG. 3 from a different perspective.

Figure 5:
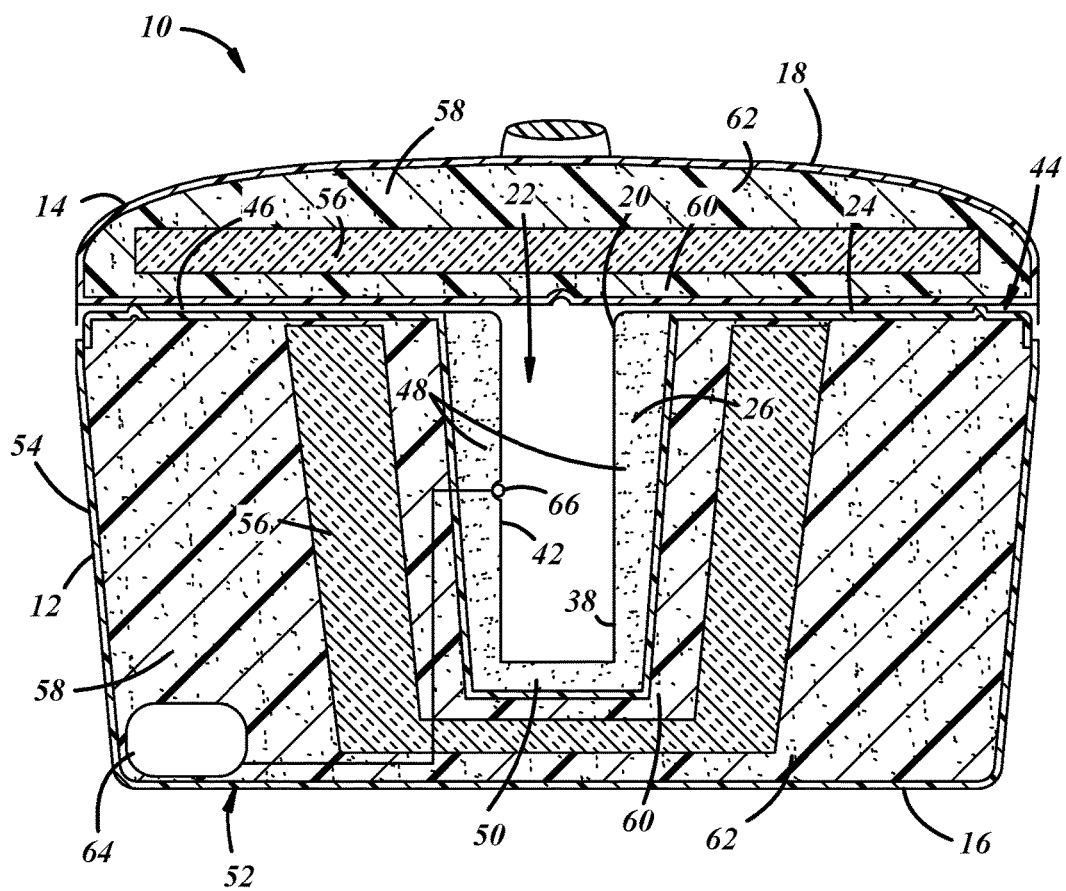
FIG. 5 is a cross-sectional view of an example of the portable cryogenic storage container in the closed condition.

FIG. 5 is a cross-sectional view of the container 10 with the retraction device and associated recess and grooves omitted. Many of the above-described elements are labeled in FIG. 5, along with a second portion 52 of the bottom 12 of the container 10. This second portion 52 includes a lower shell portion 54, which together with the upper shell portion 46, forms the outer shell 16 of the container bottom 12.

Each of the bottom 12 and top 14 of the illustrated container 10 includes at least one super-insulating layer 56 encapsulated in a foam material 58. Together, the super-insulating layers 56 and foam materials 58 fill the entire hollow outer shell 18 of the top 14 of the container 10 and the entire volume defined by the outer shell 16 and the cavity walls 48, 50 of the bottom 12 of the container. Each shell 16, 18 may be formed from a thermoplastic material or any other suitable material. A thermoplastic or other polymeric shell facilitates a lightweight and portable container different from conventional heavy, metal-based dewar constructions.

The foam material 58 may be or include polyurethane foam, or it may include or be formed from other types of foam such as expanded polystyrene (EPS) or foamed olefinic materials, for example. The foam material 58 may be an insulating material such as polyurethane foam but is not necessarily a super-insulating material. Each super-insulating layer 56 has a thermal conductivity that is less than 0.02 W/m-K, while an insulating material is any material having a thermal conductivity of 0.1 W/m-K or less. In one embodiment, each super-insulating layer 56 is formed from an aerogel blanket or panel. Aerogel materials are super-insulating at atmospheric pressure and, as such, enable construction of a super-insulated container 10 without the use of vacuum panels, which conventional cryogenic dewars typically employ. Vacuum panels typically require stronger, heavier materials such as metal to withstand the vacuum and lose most of their insulating properties if the vacuum is lost, often unbeknownst to the user. Other microporous insulating panels, some of which are super-insulating at atmospheric pressure, may also be used. Of course, it is also possible to use a vacuum panel as the super-insulating layer 56.

The storage cavity 22 in this example is defined by sidewalls 48 that circumscribe the cavity (when viewed from the top or bottom) and the bottom wall 50. In this example, each wall 48, 50 is formed from the layer 26 of porous material configured to absorb the cryogenic coolant. In some cases, only opposing sidewalls, preferably the longer sidewalls, are formed from or include the layer 26 of porous material configured to absorb the cryogenic coolant.

The porous material has a bulk volume defined by its external dimensions. The bulk volume consists of pores distributed within a solid material. The pores are voids or empty space within the bulk volume of the material. The porous material has a porosity defined as the ratio of the void volume to the bulk volume of a given portion of the material. The type of porous material contemplated here is an open-cell structure in which the pores are interconnected throughout the material, meaning that a low viscosity fluid can flow from pore to pore within the material from any one portion of the material to any other portion of the material. The pores should also be sized so the porous material has an affinity for the particular cryogenic coolant to be used. For instance, pores that are too small may prevent absorption of the cryogenic coolant, depending also on fluid viscosity and surface tension effects. The pores should also be sized to induce a wicking effect or capillary action within the material so that the cryogenic coolant is absorbed by the porous material without external pressure being applied. Pores that are too large may not promote the absorption effect.

One suitable porous material is calcium silicate. Calcium silicate is conventionally used in high temperature insulation applications rather than cryogenic applications. It has surprisingly been found that calcium silicate can provide a suitable porosity and pore size for absorption of a cryogenic coolant such as liquid nitrogen. The porosity of the calcium silicate may be about 90%. In other examples, the porous material is a super-insulating material such as an aerogel or a microporous material. Certain super-insulating materials may be particularly suitable for use as the cryogenic coolant-absorbing material of the storage container described herein because one of the characteristics of these types of materials that provides their high insulation properties—namely, the high porosity—can also provide the desired coolant absorption characteristic for the walls 48, 50 of the storage cavity 22. The porous material may have a porosity of 75% or more, a porosity of 90% or more, or a porosity of 95% or more.

The porous material may also be formed from a non-polymeric material or an inorganic material. Certain polymeric foams may be unsuitable for absorption of cryogenic coolants due to the drastic change in pore size that can occur because of high coefficients of thermal expansion. The porous material may include an inorganic oxide, such as silica, or may include a silicate other than calcium silicate. Such mineral-derived materials are able to withstand extreme temperature changes without appreciable changes in the pore structure or in the size of the component constructed therefrom, thereby eliminating problems with internal stresses that would otherwise be induced with high CTE materials like polymers.

The storage cavity 22 is sized and shaped to accommodate a cassette or other contents container in which the product intended to be stored cryogenically is contained. The walls 48, 50 define the cavity 22 and are surrounded by the foam material 58 at the outer sides of the walls facing away from the cavity. The foam material 58 provides physical support for the walls 48, 50. The foam material 58 may also provide a fluid barrier for containing the coolant within the cavity 22 and within the porous material of the walls. For instance, the foam material may be a closed cell foam material and/or have a skin layer formed at an interface with the walls 48, 50.

The illustrated container bottom 12 includes an inner layer 60 of foam material between the layer of porous material and the super-insulating layer 56, as well as an outer layer 62 of foam material between the super-insulating layer and the shell 16, such that the super-insulating layer 56 is at least partially or entirely encapsulated in the foam material 58. Similarly, the illustrated container lid 14 includes an inner layer 60 of foam material between the storage cavity 22 and the super-insulating layer 56 of the lid, as well as an outer layer 62 of foam material between the super-insulating layer of the lid and the shell 18, such that the super-insulating layer is at least partially or entirely encapsulated in the foam material 58.

The container 10 may also include an integrated data logging, data storage, and/or tracking device (e.g., a GPS device) 64 which may be built into the container 10, such as in a cavity or recess formed in the top or bottom of the container. The device 64 is shown in FIG. 5 as a combined module, but may be provided separately. The integrated device may also include a wireless transceiver configured to transmit temperature and/or location information or other stored or collected data to a receiving unit separate from the container. Such a transceiver may also be provided as part of the container separately from the storage, logging, and/or tracking device(s).

The container 10 may also include a temperature sensor 66, such as a thermocouple or thermistor, arranged to measure the temperature of the storage cavity and/or a wall of the storage cavity. The sensor 60 and/or a connector extending from the sensor to the data logging device may be built into one of the walls or porous material and/or extend through the foam material 58 and/or the super-insulating layer 56. An end of the sensor 66 may reside in a recess formed along one of the walls 48, 50 that define the cavity 22.

The illustrated container 10 also includes a vent 68. The vent 68 fluidly connects the storage cavity 22 to the external environment of the container 10 and may include one or more gas flow channels formed in or through any of the material layers of the container 10. In this case, the vent 68 comprises a recess formed in the outer shell 18 of the lid 14. The vent 68 may be configured to permit the vaporized cryogenic coolant to be transported from the storage cavity 22 to a location outside the storage container 10 when there is cryogenic coolant in the storage container, the storage cavity is closed, and the pressure inside the storage cavity exceeds a threshold value. The vent 68 may simply be a through-opening, in which case the threshold value is ambient atmospheric pressure. The vent may also comprise a one-way valve to prevent atmospheric gases from entering the storage cavity. Such a valve may be configured to open when storage cavity pressure exceeds the threshold pressure and to close when storage cavity pressure falls below the threshold pressure. Preferably, the threshold pressure is above atmospheric pressure so that vaporized coolant is not unnecessarily bled from the container, which would reduced the length of time the storage cavity is kept at the desired cryogenic temperature. In the example of FIG. 1, an end of the vent 68 at the exterior of the container is shown built-in to the lid 14 and passing through the shell 18.

In an exemplary method of using the cryogenic storage container, the container is conditioned for use prior to loading contents into the storage cavity for cryogenic storage. One method of conditioning may be referred to as the fill method, and another method of conditioning may be referred to as the cassette method.

In the fill method, the storage cavity of the container is at least partially filled with the cryogenic coolant in liquid form, either by a user or a remotely controlled device. The liquid coolant is absorbed by the porous material of the walls defining the cavity. The wall geometry, thickness, and surface area may be configured to allow absorption of all of the liquid coolant when the cavity is initially completely filled by the coolant. After the coolant is absorbed by the walls of the cavity, the container becomes what may be referred to as a dry vapor container, meaning that there is no longer any liquid within the container. When the liquid coolant has been absorbed by the walls, it begins to boil off and change to the vapor phase and result in a refrigeration effect within the storage cavity. The container is ready for use after the liquid coolant has saturated the porous material of the walls and/or after the storage cavity no longer contains liquid coolant. With liquid nitrogen as the coolant and calcium silicate as the porous wall material, saturation can occur within about 5 minutes after filling the cavity with the coolant. At this point the container can be loaded with cassettes or other materials requiring transport.

In the cassette method, cryogenically chilled or "frozen" cassettes are provided as removable and replaceable walls that at least partially define the storage cavity of the container. These cassettes comprise the coolant absorbing porous material and are stored in a non-portable cryogenic freezer where they absorb liquid cryogenic coolant. These frozen cassettes may be stored in the cryogenic freezer for indefinite periods of time and will remain at cryogenic temperatures as long as the freezer contains liquid coolant. This method allows for simplified conditioning of the cryogenic storage container, as the user does not need to pour liquid coolant directly into the storage cavity of the container.

In one example of preparing the cryogenic storage container for use with the cassette method, a pair of cryogenically frozen cassettes are removed from the non-portable cryogenic freezer and placed into the bottom 12 of the container 10, which in this case is configured to receive the cassettes as sidewalls 48 of the storage cavity. One or more contents cassette may then be placed between the frozen cassettes of porous material which have the coolant absorbed therein.

As shown in FIG. 5, the walls containing the porous material may be configured to enhance isothermal efficiency. During the fill method of conditioning, the liquid coolant may be absorbed more readily by the porous material at the closed end of the storage cavity. As the portion of the walls proximate the closed end of the cavity becomes saturated, the liquid coolant will also be absorbed toward the open end of the cavity as a result of both direct absorption and wicking or capillary action within the porous material.

Once the liquid coolant has fully saturated the porous material, it will begin to boil off and change to the vapor phase. The open end of the cavity will be subject to greater heat transfer into the cavity. As a result, the boil off of the coolant will be greater near the open end of the cavity, and the open end of the cavity may thus tend to be at a higher temperature than the closed end of the cavity. Where it is desired to provide the entire cavity with a uniform temperature between the open and closed ends, the wall thickness of the porous material may be made non-uniform as shown in FIG. 5. Here, the walls 48 are configured with a wall thickness at the open end of the cavity that is greater than a wall thickness at the closed end of the cavity. The thicker portions of the walls near the open end of the cavity thus have a larger coolant capacity and are able to provide a uniform temperature within the cavity as the nitrogen boils off. Another way to describe this is to say that the wall thickness is configured to provide greater in-wall coolant storage in the areas which will have higher rates of heat transfer. This configuration can provide a desirable isothermal or near isothermal condition within the cavity.

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A cryogenic storage container, comprising one or more walls that together define a closable storage cavity, wherein at least one of the walls comprises a layer of porous material configured to absorb a cryogenic coolant and to release the cryogenic coolant in vapor form into the storage cavity,
   wherein the porous material lines the storage cavity and is a non-polymeric material having an open-cell structure in which pores are interconnected throughout the material.

2. A cryogenic storage container as defined in claim 1, further comprising a super-insulating layer, wherein the layer of porous material is located between the super-insulating layer and the storage cavity.

3. A cryogenic storage container as defined in claim 1, further comprising a layer of material that is super-insulating at atmospheric pressure, wherein the layer of porous material is located between the layer of super-insulating material and the storage cavity.

4. A cryogenic storage container as defined in claim 1, wherein said layer of porous material comprises calcium silicate.

5. A cryogenic storage container as defined in claim 1, wherein said layer of porous material comprises a super-insulating material.

6. A cryogenic storage container as defined in claim 1, wherein said layer of porous material has a non-uniform thickness.

7. A cryogenic storage container as defined in claim 1, wherein said layer of porous material has a thickness at an open end of the storage cavity that is greater than a thickness at a closed end of the storage cavity.

8. A cryogenic storage container as defined in claim 1, wherein said layer of porous material is removable and replaceable.

9. A cryogenic storage container as defined in claim 1, further comprising a layer of super-insulating material encapsulated in a foam material, wherein said layer of porous material defines at least a portion of the storage cavity and is located between the storage cavity and the encapsulated super-insulating material.

10. A cryogenic storage container as defined in claim 1, further comprising a layer of aerogel material encapsulated in a polyurethane foam material, wherein said layer of porous material comprises calcium silicate and is located between the storage cavity and the encapsulated aerogel material.

11. A cryogenic storage container as defined in claim 1, further comprising a fluid barrier layer configured to contain the cryogenic coolant within the layer of porous material and/or within the storage cavity.

12. A cryogenic storage container as defined in claim 1, wherein the cryogenic storage container does not include a vacuum panel.

13. A cryogenic storage container as defined in claim 1, further comprising a data storage device and/or a locator device.

14. A cryogenic storage container as defined in claim 1, further comprising a temperature sensor adapted to measure the temperature of the cavity and extending at least partially through one of the walls.

15. A cryogenic storage container as defined in claim 1, further comprising a retraction device adapted to remove a cassette from the storage cavity.

16. A cryogenic storage container as defined in claim 1, further comprising a vent configured to permit the cryogenic coolant to be transported from the storage cavity to a location outside the storage container when there is cryogenic coolant in the storage container, the storage cavity is closed, and the pressure inside the storage cavity exceeds a threshold value.

17. A cryogenic storage container as defined in claim 1, wherein the layer of porous material has a porosity of at least 75%.

18. A cryogenic storage container as defined in claim 1, wherein the layer of porous material is formed from an inorganic material.

19. A method of cryogenically storing a product, comprising the step of housing the product in a storage cavity of a portable storage container comprising a liquid cryogenic coolant absorbed by a non-polymeric porous wall that lines the storage cavity and releases the cryogenic coolant in vapor form into the storage cavity.

20. The method of claim 19, further comprising the step of introducing the cryogenic coolant to a porous layer of the wall while the porous layer is attached to the portable storage container and before the product is housed in the storage cavity.

21. The method of claim 19, further comprising the step of assembling a porous layer to a portion of a storage container comprising a super-insulating layer, wherein the porous layer includes the absorbed cryogenic coolant during the step of assembling.

\* \* \* \* \*